United States Patent [19]

Wild

[11] Patent Number: 5,738,812
[45] Date of Patent: Apr. 14, 1998

[54] PROCESS FOR THE MANUFACTURE OF BREAST PROSTHESES

[75] Inventor: Helmut Wild, Neubeuern, Germany

[73] Assignee: Amoena Medizin-Orthopädie-Technik GmbH, Raubling, Germany

[21] Appl. No.: 784,620

[22] Filed: Jan. 21, 1997

Related U.S. Application Data

[63] Continuation of Ser. No. 409,988, Mar. 24, 1995, abandoned.

[30] Foreign Application Priority Data

Apr. 15, 1994 [DE] Germany ............................ 44 13 076.7

[51] Int. Cl.$^6$ ............................ B29C 41/04; B29C 41/06
[52] U.S. Cl. ............................ 264/102; 264/267; 264/310; 264/311; 264/DIG. 6
[58] Field of Search ............................ 264/46.8, 102, 264/138, 222, 255, 266, 267, 310, 311, 503, 554, DIG. 30, DIG. 53, DIG. 6

[56] References Cited

U.S. PATENT DOCUMENTS

| | | | |
|---|---|---|---|
| 4,172,298 | 10/1979 | Rechenberg | 3/36 |
| 4,238,537 | 12/1980 | Kerr | 264/310 |
| 4,247,351 | 1/1981 | Rechenberg | 156/221 |
| 4,249,975 | 2/1981 | Rechenberg | 156/245 |
| 4,298,998 | 11/1981 | Naficy | 3/36 |
| 4,356,573 | 11/1982 | Knoche | 3/36 |
| 4,428,082 | 1/1984 | Naficy | 3/36 |
| 4,836,963 | 6/1989 | Gilman, Jr. | 264/45.7 |
| 4,992,312 | 2/1991 | Frisch | 428/35.7 |
| 5,229,045 | 7/1993 | Soldani | 264/41 |
| 5,324,472 | 6/1994 | Page et al. | 264/310 |
| 5,336,263 | 8/1994 | Ersek et al. | 623/11 |
| 5,376,117 | 12/1994 | Pinchuk et al. | 623/8 |

*Primary Examiner*—Angela Y. Ortiz
*Attorney, Agent, or Firm*—Evenson, McKeown, Edwards & Lenahan, PLLC

[57] ABSTRACT

For the manufacture of breast prostheses from a shell-shaped body made from an addition-vulcanising two-component silicone rubber mass, which body is enclosed in a plastic sheet sheathing said body, a filler of fairly low density composed of hollow spheres or microspheres is added to the two-component silicone rubber mass. The mixture is filled into a sheath of plastic sheet and is cured in a mould under the effect of heat. To obtain the most uniform distribution possible of the filler in the prosthetic body, the mould filled and degassed in the customary way is turned continuously through one or two axes before and during the curing of the two-component silicone rubber mass until the silicone rubber is vulcanised to such an extent that any rising of the filler materials is prevented.

10 Claims, No Drawings

PROCESS FOR THE MANUFACTURE OF BREAST PROSTHESES

This is a continuation application of Ser. No. 08/409,988, filed on Mar. 24, 1995, now abandoned.

FIELD OF THE INVENTION

The invention relates to a process for the manufacture of breast prostheses from a shell-shaped body made from an addition-vulcanising of a two-component silicone rubber mass, which body is enclosed in a plastic sheet sheathing said body, where a filler of fairly low density composed of hollow spheres or microspheres is added to the two-component silicone rubber mass, the mixture is filled into a sheath of plastic sheet and is cured in a mould under the effect of heat.

BACKGROUND OF THE INVENTION

Breast prostheses of this type are known from German registered design 92 01 918. These breast prostheses are manufactured in the customary process in which the two components of the silicone rubber mass are set as regards their viscosity in such a way that they can be pumped and lead through a mixer together with the filler for the filling of the plastic sheets already sealed together for the prosthesis sheaths. To allow pumping, the two components and/or the mixture must possess a relatively low viscosity which results in the lighter filler spheres rising before they cure in the pouch-shaped plastic sheaths placed in the moulds so that the uniform distribution of the filler in the silicone robber mass is lost and the filler from the lower portions of the mixture migrates to the top and collects at the upper portion of the pouch-shaped plastic sheaths.

OBJECT OF THE INVENTION

It is the object of the invention to propose a process of the type given above in which light prostheses can be manufactured with an essentially more uniform distribution of the filler in the prosthetic body.

DESCRIPTION OF THE INVENTION

This object is solved in accordance with a first proposal in that the mould, filled and degassed in the customary way, is turned continuously through one or two axes before and during the curing of the two-component silicone rubber mass until the silicone rubber is vulcanised to such an extent that rising of the filler materials is prevented.

In accordance with a second proposal, the two components of the silicone robber mass can, for example, be mixed with the filler and set as regards their viscosity in such a way that the mixture has a viscosity of 1,800 to 2,200 mPa. If the mixture of the silicone robber mass and filler possesses a viscosity prior to its curing of 1,800 to 2,200 mPa and a viscosity of around 2,000 mPa, it is so viscous that the filler spheres cannot rise noticeably until their curing so that the desired uniform distribution of the filler materials of the mixture is maintained in the mixture and also later in the cured prosthesis.

The components of silicone rubber customarily used in the manufacture of breast prostheses comprise a mixture of a polymer, silicone oil, an inhibitor, a vulcanising agent and a coloured paste with a catalyst being used. Here, during their processing the components have a viscosity of around 500–600 mPa with a pot life of 4 to 5 hours at room temperature. The polymer comprises a vinyl shortstopped linear polydimethyl siloxane (dimeticon). Polydimethyl siloxane without functional groups is used as the silicone oil. The silicone oil serves to dilute the components. A platinum catalyst is used as the catalyst. The vulcanising agents are polysiloxanes with silicon bound hydrogen atoms. A coloured pigment mixture can be used, advantageously added to the silicone oil, solely to improve the appearance.

To manufacture the light prostheses in accordance with the second proposal, the filler is added to one or preferably both components of the silicone rubber mass and stirred into the components and mixed using a static or dynamic mixer and then filled into the prepared plastic sheath consisting of two sealed sheets. The plastic sheath filled in this way is placed into a mould in the customary way and cured in this. The filling aperture in the sheath circumference can be sealed after the filling or during curing.

The filler can comprise hollow spheres or also light-solid spheres made from another suitable material.

In one modification of the process in accordance with the invention the customary components given above of the silicone rubber are used, but the two components are set in such a way that the silicone rubber filler mixture possesses a viscosity of around 2,000 mPa.

In accordance with a third proposal the two components of the silicone rubber mass can, for example, be mixed with the hollow spheres or microspheres and set as regards their viscosity in such a way that the mixture has a viscosity of 400–800 mPa, where by using catalysts and by adding vulcanising agents the mixture is designed in such a way that these pregel so much after only 3 to 6 minutes that the filler materials can no longer rise. In this process, the two components of the silicone rubber mass initially only have such a low viscosity that the components and the mixture can be pumped into the prepared plastic sheaths by normal pumping. To obtain this primping capability, the viscosity of the mixture of silicone rubber and filler is around 400–800 mPA and preferably about 500–700 mPa. By the use of suitable catalysts and vulcanising agents the mixture gels at room temperature after only 4 to 6 minutes and preferably after 5 minutes so that rising of the filler materials is prevented and the desired uniform distribution of the filler in the silicone rubber is maintained.

In accordance with a further proposal for the manufacture of light prostheses, the two components of the silicone rubber mass are thixotroped so that the filler essentially cannot rise until the curing of the silicone rubber mass. The desired thixotropic behaviour of the two fluid components can be achieved, for example, by adding silicic acid or silica powder to the mixture.

In accordance with a further process for the manufacture of light prostheses, a filler comprising microspheres which has around the same density as the silicone rubber mass is added to the customary components of the silicone rubber mass of customary viscosity, but where the microspheres of the filler only swell due to the heat during the curing of the prosthetic body. As, therefore, the microspheres used as fillers initially have the same density as the silicone rubber mass prior to its curing, the filler does not tend towards undesired rising. During curing, however, the microspheres swell while being reduced in density at a time where the silicone rubber mass has already gelled to such an extent that these can no longer rise.

I claim:

1. A process for the manufacture of a solid breast prosthesis made from a mixture comprising an addition-vulcanized two-component silicone rubber mass and a filler of substantially low density, said filler comprising hollow spheres or microspheres, wherein the mixture is enclosed in a plastic sheet sheathing and cured by heating in a mold to form body of the breast prosthesis, comprising the steps:

filling the mold with the mixture enclosed in the plastic sheet sheathing;

degassing the mixture in the mold;

turning the filled mold continuously through one or two axes before and during curing of the mixture;

curing the mixture until the mixture is vulcanized sufficiently that rising of the filler is prevented, and an even distribution of the filler is achieved, thereby forming the solid breast prosthesis.

2. The process for the manufacture of a solid breast prosthesis according to claim 1, characterised in that:

the two components of the silicone rubber mass are mixed with the hollow spheres or the microspheres, wherein the mixture so formed has a sufficiently high viscosity that the filler cannot substantially rise in the mixture before or during curing.

3. The process according to claim 2, characterised in that:

the two components of the silicone rubber mass are mixed with the hollow spheres or the microspheres, wherein the mixture so formed has a viscosity of 1,800 mPA to 2,200 mPA.

4. The process for the manufacture of a solid breast prosthesis according to claim 1, characterised in that:

the two components of the silicone rubber mass are mixed with the hollow spheres or the microspheres and, by addition of catalysts and vulcanising agents, the mixture so formed pregels before the filler rises.

5. The process according to claim 4, characterised in that:

the two components of the silicone rubber mass are mixed with the hollow spheres or the microspheres, wherein the mixture so formed has a viscosity of about 400 mPA to 800mPA, and that, by the addition of catalysts and the addition of vulcanising agents, the mixture pregels sufficiently after 3 minutes to 6 minutes that the filler can no longer rise.

6. The process for the manufacture of a solid breast prosthesis according to claim 1, characterised in that:

the two components of the silicone rubber mass are thixotroped, wherein rising of the filler is substantially prevented before curing of the silicone rubber mass.

7. A process for the manufacture of a solid breast prosthesis made from a mixture comprising an addition-vulcanizing two-component silicone rubber mass and a filler comprising microspheres, wherein the mixture is enclosed in a plastic sheet sheathing to form a body of the solid breast prosthesis, comprising the steps of:

mixing the two components of the silicone rubber mass with the microspheres, wherein said microspheres have substantially a same density as the silicone rubber mass and wherein said microspheres only swell due to the effect of heat during curing;

filling the mixture into the plastic sheet sheathing; and curing the mixture in the plastic sheet sheathing in a mold until an even distribution of the filler in the sheathing is achieved and further swelling of the filling is prevented.

8. The process according to claim 3, wherein the mixture has a viscosity of about 2000 mPA.

9. The process according to claim 5, wherein the mixture has a viscosity of about 500 mPA to 700 mPA.

10. The process according to claim 5, wherein the mixture pregels sufficiently after about 5 minutes that the filler can no longer rise.

* * * * *